Figure 3:
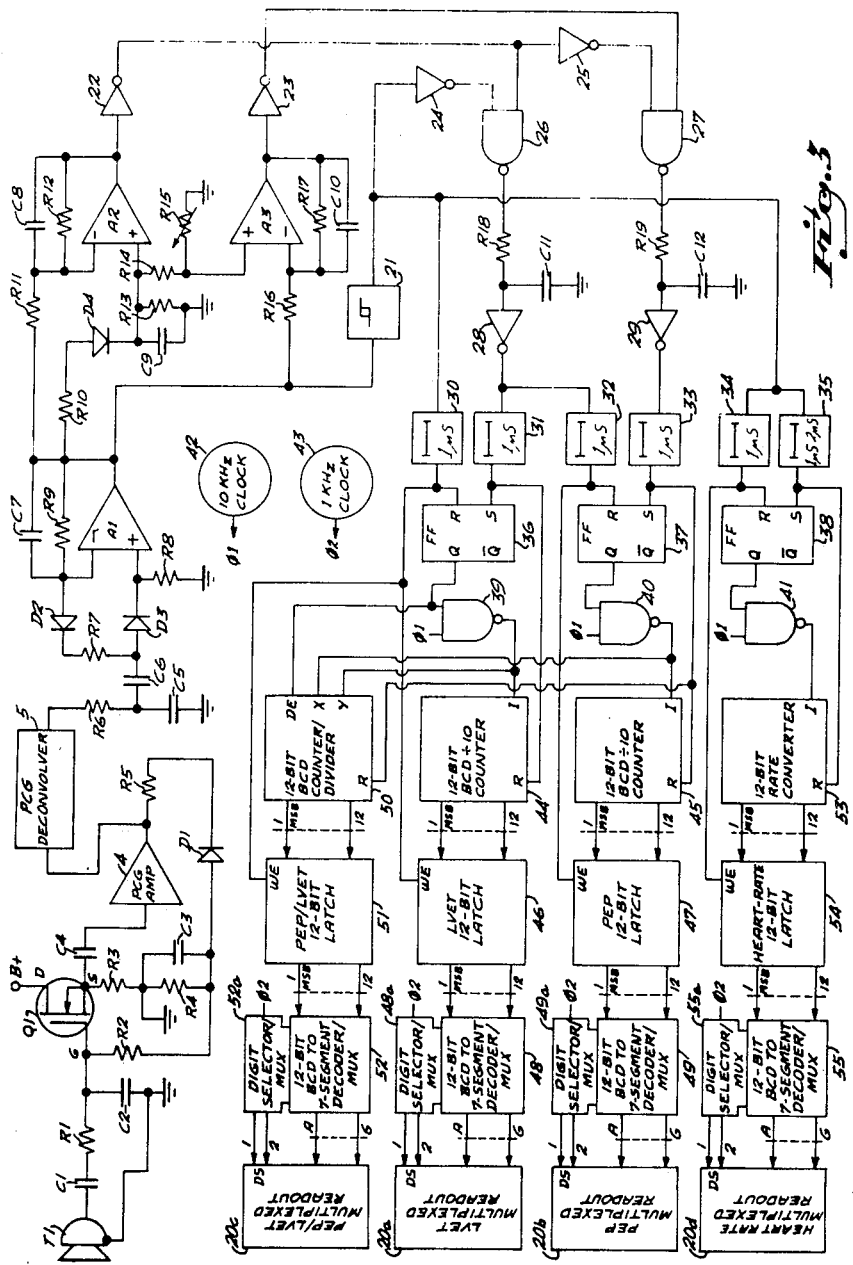

United States Patent [19]

Cormier

[11] 4,289,141
[45] Sep. 15, 1981

[54] METHOD AND APPARATUS FOR EXTRACTING SYSTOLIC VALVULAR EVENTS FROM HEART SOUNDS

[75] Inventor: Denny C. Cormier, Miami, Fla.

[73] Assignee: Cormier Cardiac Systems, Inc., Miami, Fla.

[21] Appl. No.: 34,688

[22] Filed: Apr. 30, 1979

Related U.S. Application Data

[63] Continuation of Ser. No. 813,248, Jul. 7, 1977, abandoned, which is a continuation-in-part of Ser. No. 715,895, Aug. 19, 1976, Pat. No. 4,094,308.

[51] Int. Cl.³ .............................................. A61B 00/00
[52] U.S. Cl. ................................................... 128/713
[58] Field of Search ............... 128/696, 701, 713, 715, 128/695

[56] References Cited

U.S. PATENT DOCUMENTS

| | | | |
|---|---|---|---|
| 3,776,221 | 12/1973 | McIntyre | 128/672 |
| 3,831,590 | 8/1974 | Boyce et al. | 128/713 |
| 3,841,313 | 10/1974 | Wesseling et al. | 128/713 |
| 3,881,481 | 5/1975 | Heole et al. | 128/713 |
| 4,004,575 | 1/1977 | Gähwiler et al. | 128/713 |
| 4,137,910 | 2/1979 | Murphy | 128/713 |

OTHER PUBLICATIONS

Cousin et al., "Medical and Biological Engineering", vol. 12, No. 4, Jul. 1974, pp. 479–481.

*Primary Examiner*—William E. Kamm
*Attorney, Agent, or Firm*—Howard L. Rose

[57] ABSTRACT

A non-invasive method and means for determining beat-by-beat assessments of a patient's cardiac performance by measuring the "pre-ejection phase" (PEP) and the "left ventricular ejection time" (LVET), the aforementioned phrases also being known as the "systolic time intervals" (STI) of the heart. The system accomplishes its function through the following method: transduction of the heart sounds into an electrical phonocardiogram (PCG) signal and controlled amplification thereof; extraction of initial cardiac contraction and aortic valvular events by subjecting the PCG to the general inverse-filtering technique known as "deconvolution"; electronic separation of the PEP, LVET and heart pulse intervals from the deconvolved PCG with microcomputer circuitry comprising microprocessor and digital logic assemblies; precise measurement and simultaneous storage of the PEP, LVET, the PEP/LVET ratio, and the heart rate with the use of electronic digital counters, timers, dividers, and buffer memories after every heart beat; and finally effecting digital readout for instantly displaying the systolic time intervals, their respective ratio, and the heart rate, or for storing them for later use.

9 Claims, 8 Drawing Figures

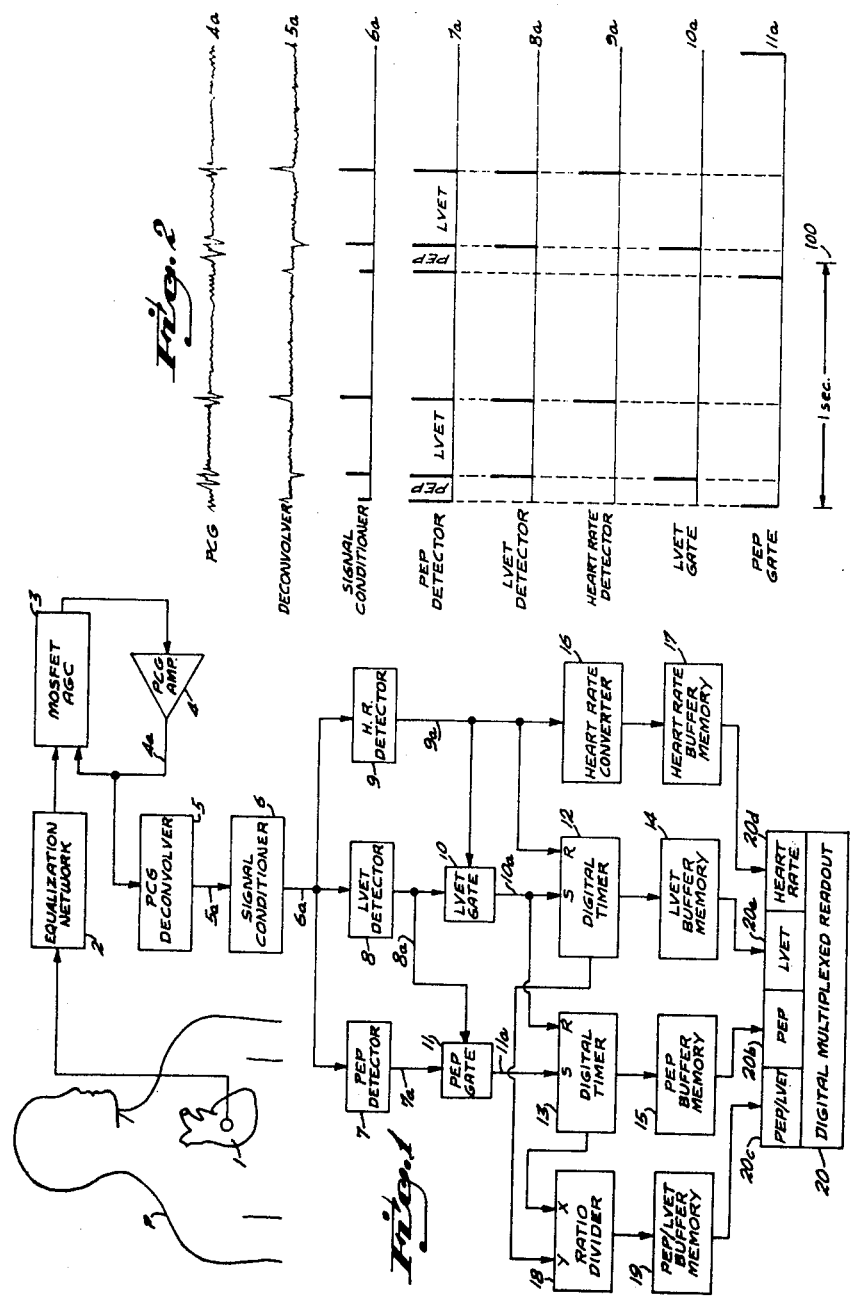

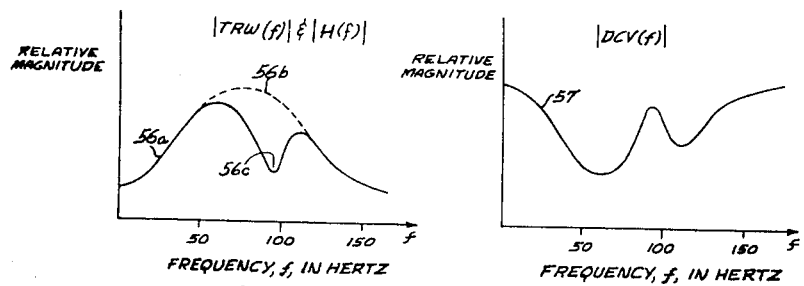
Fig. 4a
Fig. 4b
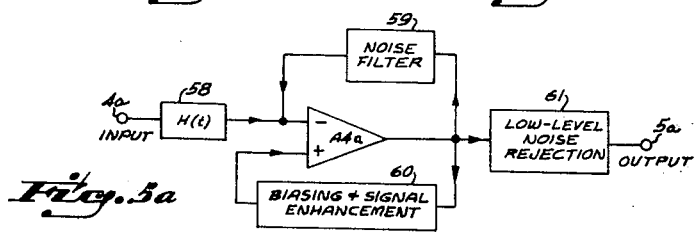
Fig. 5a
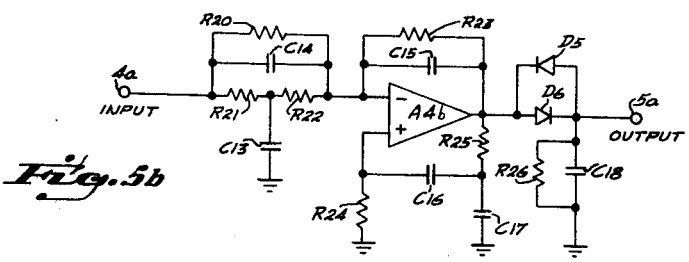
Fig. 5b
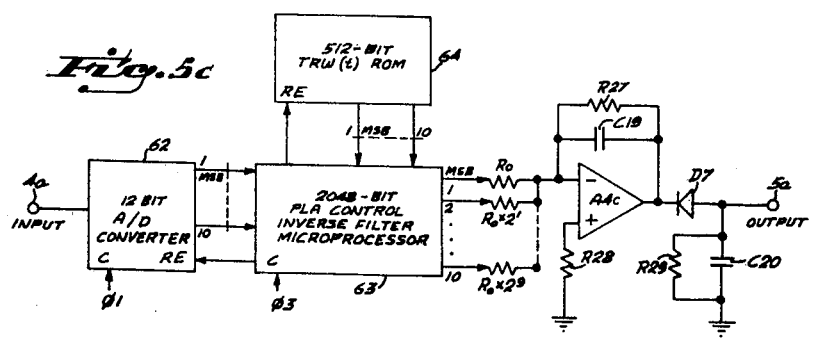
Fig. 5c

METHOD AND APPARATUS FOR EXTRACTING SYSTOLIC VALVULAR EVENTS FROM HEART SOUNDS

This application is a continuation of application Ser. No. 813,248, filed July 7, 1977, now abandoned, which was a continuation-in-part of application Ser. No. 715,895 filed Aug. 19, 1976, now U.S. Pat. No. 4,094,308.

This invention relates generally to non-invasive medical diagnostic methods and systems or devices in cardiology. More specifically, this invention relates to a method and system wherein the phonocardiogram (PCG) is used exclusively to rapidly determine the systolic time intervals (STI) of the heart through use of the technique known as deconvolution. The invention accomplishes its function without invading the body of the patient.

Non-invasive methods, and devices or systems for cardiac diagnostics have taken many forms. Presently, the most recognized and utilized procedure is electrocardiography or the ECG. Despite its popularity, the ECG has frequently proven to be an insufficient measure of cardiac performance, since it only manifests electrophysiology of the heart, providing little or no information on myocardial and valvular deterioration, or on hemodynamic abnormalities. To supplement this shortcoming in the ECG, several prior art stethoscopic devices have been developed over the years to assist the physician with prompt auscultative of the heart sounds or phonocardiogram (PCG). Most of these devices and their respective principles of operation rely upon passive mechanical or electromechanical means for facilitating sound transmission to the ear by increasing acoustical compliance and attenuating high or low frequencies. Others simply amplify the PCG with a standard audio amplifier. Although these methods, systems and devices facilitate the aural evaluation capabilities of a physician, they cannot overcome the basic physiological fact that a large part of the sound energy contained within the PCG is clustered around frequencies below the range of human audition. Still other prior art devices electronically evaluate gross anomalies in the PCG, such as murmurs, galloping sounds, and arrhythmias, by merely systematizing standard auscultative procedures. While previous contrivances in this category sometimes prove valuable for isolation of pronounced abnormalities, they are generally unable to detect the vast majority of cardiac patients whose symptomatology is often very subtle in nature. The method and device of the present invention utilizes the deconvolution technique to extract the display intrinsic information from the PCG on valvular and contractile events that reflect a consistent measure of cardiac performance.

As a tool in geophysics, deconvolution has proven valuable in the restoration of geodynamic events contained within the sonic vibrations of a seismogram. Advanced acoustical studies have shown that a pulsed mechanical or electromechanical system will transmit a sonic wavefront to the surronding media and that the same sonic wavefront will undergo transformation peculiar to the medium of transmission. In an analogous fashion, the method and system of the present invention apply the techniques of deconvolution toward rapid phonometric analysis of the phonocardiogram by precisely isolating valvular and contractile events during cardiac systole, thereby enabling their measurement in the determination of the systolic time intervals to a high degree of accuracy.

Measurement of the systolic time intervals provides a consistent indicator of cardiac performance that the ECG and simply auscultative procedures lack. Moreover, the STI represent a simultaneous measure of both electrodynamic and mechanical parameters involved with systolic action. For this reason, application of the STI as a diagnostic aid is steadily gaining recognition among the general medical community. While there are several subcategories of systolic time intervals presently in use, the ones of major interest are: (1) the "pre-ejection phase or period" (PEP), which is the elapsed time from Q-wave onset in the ECG whereupon ventricular contraction commences, to the opening of the aortic valve; (2) the "left ventricular ejection time" (LVET), which is simply the length of time the aortic valve remains open.

Viewed clinically, a lengthening of the PEP usually results from a reduction in contractile capacity of the myocardium or a decrease in vascular elasticity. Conversely, a shortening of the LVET is an indication of deteriorating vascular integrity and a weakening of the myocardium thereby diminishing the ventricular stroke volume and ejection fraction. In a healthy cardiovascular system, the supine PEP/LVET ratio remains a relatively constant 0.34 to 0.36 over a wide range of heart rates. An increase of twenty to fifty percent in the PEP/LVET ratio reflects an impairment of cardiac function and is generally traceable to nervous and muscular tissue damage frequently accompanying ischemic or sclerotic conditions in the heart wall. Diminution of the PEP/LVET ratio, although uncommon, is usually associated with valvular insufficiencies, as for example, aortic stenosis or regurgitation. More acute conditions, such as myocardial infarction and diseases of the left ventricle are always accompanied by significant enlargement of the PEP/LVET ratio. (For a detailed discussion of the use of the STI for diagnostic purposes reference may be made to the article of Chapter 6 in *PROGRESS IN CARDIOLOGY*, entitled "The Systolic Time Intervals As A Measure of Left Ventricular Performance In Man" by A. M. Weissler, M.D. et al, published by Lea and Febiger, Philadelphia, Pa., copyright 1972.)

The conventional means for measuring the systolic time intervals has been to employ simultaneous ECG, PCG, and plethysmographic (pulse wave) tracings, which required an expensive array of instrumentation together with specially trained medical technicians to record and analyze the results. In practice, the bulk of STI determinations have been made by comparing the ECG and plethysmogram alone, the PCG, because of its complexity, having heretofore been used only as an approximate ancillary check against the plethysmogram to locate in time aortic valvular events or gross irregularities in the heart sound. Aside from the oftentimes prohibitive expense and lengthy time requirements, this previous method has not been altogether reliable. Most inaccuracies have arisen from improper placement of the plethysmographic transducer, whereupon timing errors have developed in the ensuing plethysmogram. Further errors have also occurred as a consequence of variations in judgment by different medical technicians required to visually evaluate graphical or oscillographic records to determine the particular STI of interest. As a result, measurement of the STI has not heretofore been generally recognized as a routine supplemental or alternative diagnostic procedure to that of stethoscopic or the ECG recording method of cardiac evaluation.

It is the general object of this invention to provide an improved non-invasive method and system (device) for rapidly measuring the systolic time intervals (STI) of the heart for diagnostic purposes by deconvolution of the phonocardiogram (PCG).

It is another object of this invention to provide a non-invasive method and system or device for rapidly measuring the particular systolic time intervals (STI) of the heart, hereinafter known as the PEP and LVET, wherein they are displayed in a digital form with a high degree of artifact supression and reliability that is a significant improvement over previous comparable methods and devices.

It is another object of this invention to provide a non-invasive method and system for rapidly measuring the PEP, LVET and the PEP/LVET ratio, wherein they are displayed in a digital form and automatically evaluated with constant preset criteria through the use of miniaturized linear and digital integrated circuitry along with miniaturized large-scale-integration (LSI) microprocessor circuitry, thereby permitting the construction of an extremely portable device which may even operate on battery power whenever or wherever conventional sources of electricity are unavailable.

These objects are accomplished in the preferred embodiment by completely eliminating the need for the ECG and plethysmogram in the measurement of the STI. Instead, the method and system of the present invention have solved the problems encountered with prior art contrivances by relying wholly upon the PCG, wherein the inverse filtering technique of deconvolution extracts initial cardiac contractile and aortic valvular events, hereinafter termed "systolic valvular events" or SVE(t), that temporally define the PEP and LVET. A PCG deconvolver, which is an integral feature of this invention, provides the deconvolution technique that is essential to the isolation of SVE(t) from extraneous vibrations indigenous to the production of the heart sounds. This deconvolution technique, morever, inherently obviates the requirement of critical placement of the PCG transducer, as is characteristic of plethysmography, echocardiography, and other instrumentation heretofore employed in the measurement of STI.

The theoretical aspects of this invention embody the fundamental physical principales whereupon the heart sounds are produced. During a cardiac contraction, various resonant structures of the myocardium undergo vibratory motion as muscle tonus and blood-flow parameters change rapidly with associated Reynolds and Froude numbers. Sound waves propagating over the inner and outer walls of the heart manifest the transient response properties characteristic of two loosely-coupled harmonic systems, wherein each opposes the action of the other. Although this vibratory activity on the myocardium is best described by a series of Bessel functions, the boundary conditions imposed by the chest wall constrain acoustical transmission to one direction and therefore confine the time-varying "transient response wavelet" or TRW(t) and the resulting heart sounds to a particular analytical form. Both theoretical and empirical phonometric studies on normal heart activity reveal that TRW(t) takes the following average analytical form:

$$TRW(t) = 3Ae^{-t/0.012} \sin 2\pi(65)t - Ae^{-t/0.015} \sin 2\pi(100)t$$

(where $A = SVE(0)$, and t is in seconds).

Appropriately, the deconvolver incorporated by the method and system of the present invention has a frequency response, $DCV(f)$, equalling $TRW^{-1}(f)$, which is the inverse of the Fourier transform for the transient response wavelet $TRW(f)$, such that the product, $DCV(f) \cdot TRW(f)$, is a constant for all frequencies between 5 and 500 hertz. Since the overall Fourier transform for the heart sounds, $PCG(f)$, equals $TRW(f) \cdot SVE(f)$, then algebraically $SVE(f) = PCG(f) \cdot TRW^{-1}(f)$, and therefore $SVE(f) = PCG(f) \cdot DCV(f)$ by substitution. Returning to the time domain, the deconvolver must then operate as follows:

$$SVE(t) = \int PCG(\tau)DCV(t-\tau)d\tau$$

where "$\tau$" is the standard "dummy variable" used in the integral deconvolution expression. Whenever the deconvolver is presented with a set of oscillations corresponding to initial cardiac contractile or valvular action, a spike of both voltage and current appears at its output.

Another important feature of this invention is its ability to suppress noise artifacts produced externally and by the deconvolution process through the use of selective low-level noise attenuation with active diode-coupled networks that also provide full-wave rectification of the SVE(t). Thereafter pulse height detection of the rectified SVE(t) is achieved with hysteretical comparators wherein digital level converters regulate extracted voltage and current pulses to trigger digital logic networks and microcomputer circuits which selectively activate electronic counters, timers, and dividers to precisely measure the PEP, LVET, the PEP/LVET ratio, and heart rate after every closing of the aortic valve. STI are then stored in buffer memories and displayed on any conventional digital readout, or may be stored on magnetic tape for later replay or computer analysis. This invention may also be used to evaluate telemetered or pre-recorded PCG's as long as care has been taken to insure their fidelity.

Another important feature of this invention is its portability and rapid analytical capability. Small enough to be held in one hand or carried in a doctor's bag, it can be used virtually anywhere a cardiac emergency might arise. In addition, the method and system of the present invention include a high-gain PCG amplifier coupled with an automatic gain control (AGC) that permit the detection of heart sounds even through several layers of clothing, and thereby provide the physician or medical technician with an extended auscultative range along with the digital STI information. Furthermore, both PEP and LVET are evaluated by constant criteria, preset and digitized with microcomputer circuitry contained therein. The invention, therefore, eliminates errors in judgment sometimes made by technicians interpreting graphical records. The invention also allows the medical practitioner to have a complete set of reliable diagnostic data for outpatient screening or in emergency circumstances within seconds after the PCG transducer is placed in contact with the chest of the patient, regardless of whether the measurements are made in a hospital room, a doctor's office, or a remote locality, for example during a cardiac crisis where cardiovascular performance can be evaluated almost immediately after applying the phonocardiographic transducer to the chest of the patient.

An additional aspect of this invention relates to the large number of people whose heart diseases go undetected and sometimes die needlessly because diagnostic facilities to assess their cardiac conditions are either unavailable or impractical. The method and system of the present invention are much less expensive than prior instrumentation; many heart disease victims are therefore afforded a greater opportunity for survival by virtue of this invention.

The preceding and other objects, features, and advantages of the invention will be apparent from the following description of the preferred embodiment of the invention when read with reference to the drawings in which:

FIG. 1 is a block diagram of the method and system of the present invention, demonstrating the essential mechanisms of its operation;

FIG. 2 graphically depicts the various waveforms and electronic signals relating to the measurement of the systolic time intervals by the method and system of the invention;

FIG. 3 is a combined schematic and logic diagram illustrating the circuitry incorporated by the method and system of the present invention to deconvolve, extract and compute the PEP, LVET, the PEP/LVET ratio, and the heart rate from the PCG and display the results in a digital format;

FIGS. 4a and 4b, respectively, show the magnitude spectra for the transient response wavelet, $|TRW(f)|$, together with its fundamental component, $|H(f)|$, and the magnitude spectrum for the deconvolver, $|DCV(f)|$, utilized by the method and system of the present invention; and FIGS. 5a, 5b and 5c demonstrate the general principle of operation of the deconvolution system, an analog deconvolver circuit, and a digital deconvolver circuit, respectively, all of the foregoing being integrally related to the method and system of the present invention.

Referring to both FIG. 1 and FIG. 2, the entire measurement process of the method and system of the present invention, as herein disclosed, can be viewed for the purpose of relating its essential mechanisms of operation in regard to the determination of the systolic time intervals by deconvolution of the phonocardiogram (PCG). The measurement process begins when the PCG transducer 1 makes contact with the chest of a patient P whereupon acoustical energy of the heart sounds is converted into electrical energy. After conversion to an electrical signal, the PCG is then passed through an equalization network 2 which compensates for any frequency or phase distortion introduced by the PCG transducer 1 as well as attenuating high frequency voltage or current transients. A MOSFET automatic gain control (AGC) 3 works in conjunction with a high-gain monolithic PCG amplifier 4 to maintain the PCG signal at a specified level of voltage and current over a wide range of input amplitude variations.

The output of the PCG amplifier 4a, which is shown graphically in FIG. 2, is then passed to the PCG deconvolver 5, which isolates and identifies the systolic valvular events, SVE(t), in the form of electrical spikes with varying amplitudes at its output 5a. The exact nature of these spikes may be viewed in FIG. 2, wherein reference numeral 100 indicates an interval corresponding with a period of 1 second representing the typical time frame for the various signals graphically depicted.

Suppression of spurious low-level noise often accompanying the deconvolution process is accomplished with the signal conditioner 6, which also provides full-wave rectification of the deconvolver output spikes 5a. Although the signal conditioner 6 narrows the deconvolver output spikes 5a to facilitate the operation of detectors 7, 8, and 9, the amplitude character of the signal conditioner output pulses 6a remains unaffected, as indicated in FIG. 2.

Since all the information for determination of the PEP, LVET, and heart rate is still contained within the signal conditioner output 6a alone, the PEP detector 7, LVET detector 8, and heart rate detector 9, are required to separate the pulses on the basis of amplitude to establish the timing markers for measurement of the systolic time intervals and the accompanying heart rate. Separation of the timing pulses begins as the heart rate detector 9 is triggered by the largest pulse in the signal conditioner output 6a, which invariably corresponds to closure of the aortic valve and the termination of the LVET period. With a slightly lower trigger threshold than the heart rate detector 9, the LVET detector 8 is activated by both opening and closing of the aortic valve. The PEP detector 7, with the lowest trigger threshold, responds to all three systolic valvular events. To prevent false triggering, both the PEP detector 7 and the LVET detector 8 have an internal threshold control system to automatically compensate for minor fluctuations in signal levels and also employ integrated hysteretic comparator circuitry to reject high-frequency noise transients. All three of the detector outputs 7a, 8a, and 9a produce pulses of a standard amplitude corresponding to a logic level one. Final separation of the timing pulses is performed by the logic circuitry contained within the LVET gate 10 and the PEP gate 11.

With regard to the LVET gate 10, its digital logic circuit assemblies compare the LVET detector output 8a with the heart rate detector output 9a, so that an electrical logic level one pulse is generated at its output 10a only when a logic level one pulse arrives from the LVET detector output 8a alone but not from the heart detector output 9a. Thus, whenever there are simultaneous pulses from the LVET detector output 8a and heart rate detector output 9a, the LVET gate output 10a is inhibited and remains at a logical zero, thereby demarcating only the opening of the aortic valve. Similarly, the PEP gate 11 incorporates digital logic circuit assemblies identical to those of the LVET gate 10 and compares the LVET detector output 8a with the PEP detector output 7a, whereupon an electrical logic level one pulse is generated at its output 11a only when a logic level one pulse arrives from the PEP detector output 7a alone but not with coincidental pulses from the LVET detector output 8a. Hence, whenever there are simultaneous pulses from the PEP detector output 7a and the LVET detector output 8a, the PEP gate output 11a is inhibited and remains at logical zero, thereby denoting only the commencement of ventricular contraction.

The LVET gate output 10a supplies a trigger pulse which starts the electronic digital timer 12 to measure the LVET interval, resets the timing cycle of the electronic digital timer 13 that is used to measure the PEP interval, and is also carried through the digital timer 13 to momentarily enable the PEP buffer memory 15, thereby storing a new value of the PEP. The LVET interval measurement is concluded when a trigger pulse arrives from the heart rate detector output 9a which resets the electronic digital timer 12 and is also carried through the digital timer 12 to momentarily enable the LVET buffer memory 14, thereby storing a new value of the LVET. A trigger pulse from the PEP gate output 11a restarts the timing cycle of the electronic digital timer 13 to begin measuring the next PEP interval. As is hereinafter more particularly described in connection with the detailed description of FIG. 3, a ten kilohertz oscillator clock 42 coupled with digital ripple counters 44 and 45 permit both electronic digital timers 12 and 13 to accurately measure intervals of time to a tolerance of 0.1 millisecond.

An additional function of the heart rate detector 9 is to drive a heart rate converter 16, which computes the heart rate in beats per minute from the duration of the cardiac cycle. At the same time, a trigger pulse from the heart rate detector 9a is also carried through heart rate converter 16 to momentarily enable the heart rate memory buffer 17 to store the most current value for the heart rate. The ratio divider 18, which computes the PEP/LVET quotient from the contents of the electronic digital timers 12 and 13, also receives a reset command from the PEP gate 11 output 11a through digital timer 13. The PEP/LVET buffer memory 19 is also momentarily enabled by a trigger pulse from the heart rate detector output 9a, allowing storage of the most recent value of the PEP/LVET ratio.

Referring specifically now to FIG. 1, the buffer memories 17, 14, 15 and 19 are all digital storage systems which hold the values of the heart rate, LVET, PEP, and PEP/LVET, respectively, from the previous cardiac cycle for display or transmission purposes while the latest measurements are being taken. At the end of each systolic cycle, new values are transferred from electronic digital timers 12 and 13, heart rate converter 16, and ratio divider 18 in less than one microsecond. Consequently, the digital multiplexed readout 20 presents an unflickering visual display of the LVET 20a, PEP 20b, PEP/LVET 20c and H.R. 20d, wherein any or all of which may take the form of light emitting diode, electroluminescent, or liquid crystal numerals. Moreover the buffer memories 14, 15, 17 and 19 also provide transfer time for transmission of data to magnetic tape storage or high-speed printer system interfacing with conventional binary or binary-coded decimal (BCD) formats.

Referring to FIG. 3, a detailed schematic and logic diagram is depicted of the circuitry used by the system described in FIG. 1. T1 is a low-level dynamic or transformer-coupled piezoelectric PCG transducer with an output impedance between 50,000 and 100,000 ohms and a bandwidth of 1000 hertz. The input 0.033 microfarad capacitor C1 blocks direct current and all frequencies below five hertz that are generally associated with vibrational noise. Undesirable high-frequency harmonics and transient noise are controlled by the combination 1 M resistor R1 and 330 picofarad capacitor C2, which also correct frequency and phase distortion introduced by PCG transducer T1. Together C1, R1, and C2 form the equalization network 2 shown in FIG. 1. The output from the equalization network 2 connects with the very high impedance (greater than 1000 megohms) gate of the depletion type n-channel MOS field-effect transistor Q1 or simply MOSFET Q1. (MOSFET is an acronym for metal-oxide-semiconductor field effect transistor sometimes known as an insulated-gate field effect transistor or IGFET.) In addition, a negative bias signal is supplied to the gate of Q1 by the 10 M resistor R2, said resistor also being operative in series with capacitor C2 to suppress any voltage or current transients that might traverse the parallel 100 K resistor R4 and 10 microfarad capacitor C3 during turn-on or switching, although it is the express purpose of R4 and C3 to provide a one second time constant to smooth the rectified output from PCG amplifier 4 through silicon switch diode D1. Therefore, any overall gain change in the PCG amplifier output 4a exceeding the one-second time constant prescribed by R4 and C3 passing through the 10 K current limiting resistor R4 alters the charge across C3 and hence changes the negative gate bias voltage produced by source 1.8 K resistor R3 to appropriately increase or decrease the fractional gain factor of the MOSFET Q1 source follower configuration. In this manner the PCG amplifier output 4a is maintained at a uniform RMS voltage and current level within a tolerance of ±1 db wherein the foregoing feedback network starting from R5 to the gate of transistor Q1 comprises the automatic gain control (AGC) 3 shown in FIG. 1. An enhancement type MOSFET could be substituted for the depletion type MOSFET by reversing the biasing configuration of R3. A 0.033 microfarad DC blocking capacitor C4 prevents amplification of the bias voltage across R3 by the 80 db open-loop gain factor of the linear integrated circuit (IC) PCG amplifier 4 while leaving frequencies above five hertz undistorted due to the high input (one-megohm) impedance and the 1000 hertz bandwidth of said PCG amplifier.

After the output of the PCG amplifier 4 has been processed by the deconvolver 5, high-frequency noise and spurious transients are attenuated by the noise suppression network comprising the 1 K resistor R6, the 0.1 microfarad capacitor C5, the 1.0 microfarad capacitor C6, and the two 10 K resistors R7 and R8. Silicon switch diodes D2 and D3 provide full-wave rectification of the signal by supplying reversed signal polarities to the differential inputs of the high-performance frequency compensated operational IC amplifier A1. Further rejection of undesirable high frequency components beyond 500 hertz is attained at a combined slew rate of 18 db/octave through the 0.033 microfarad negative feedback capacitor C7 and the above described input noise suppression networks to operational amplifier A1. Gain for operational amplifier A1 is sustained at unity by the equality of the 10 K input resistors R7, R8, and feedback resistor R9. The 10 K resistor R10 limits current to the automatic threshold control network composed of the silicon switch diode D4, R-C time constant circuit of the 100K resistor R13 in parallel with the 10 microfarad capacitor C9, and the divider resistor R14 with a value of 10 K and R15 with a value of 1 M. R15 is a trimmer resistor set initially to optimize the performance of linear monolithic IC hysteretic comparators A2 and A3. Sensitivity of the comparators A2 and A3 is controlled by the ratio of 100 K feedback resistors R12 and R17 and the 1 K input resistors R11 and R16. The threshold trigger lag in the hysteretic comparators is provided by the 330 picofarad feedback capacitors C8 and C10.

Referring to both FIG. 1 and FIG. 3, the operational amplifier circuit A1 and its associated components provide the circuitry for the signal conditioner 6, while the hysteretic comparators A2 and A3 with their surrounding components comprise the sensing stages for the LVET detector 8 and the PEP detector 7, respectively. The Schmitt trigger 21 constitutes the circuitry for the heart rate detector 9, since the aortic pulse magnitude is controlled by the ACG 3. Digital inverters 22 and 23 supply a logical one pulse for the LVET detector output 8a and the PEP detector output 7a whenever either detector 8 or 7 has been triggered as previously described.

Logic inverter 24 and NAND gate 26 constitute the digital integrated circuitry for the input of LVET gate 10 wherein the output of the NAND gate 26 only changes state when there is a logical zero at the input of inverter 24 and a logical one at the output of inverter 22. Having identical logic circuitry to that of the LVET gate 10, the input of PEP gate 11 is comprised of logical inverter 25 and NAND gate 27 which changes state under exactly the same Boolean conditions as defined by inverter 24 and NAND gate 26. The R-C time constant established by the 100 ohm resistors R18 and R19, along with their respective 10 microfarad capacitors C11 and C12, prevent sporadic and multiple gate pulses to the inputs of logical inverters 28 and 29 which provide the LVET gate output 10a and the PEP gate output 11a, respectively. Additionally, the values for the R-C networks R18–C11 and R19–C12 have been selected to be compatible with either TTL or CMOS digital integrated circuitry.

Inasmuch as identical logic circuitry is employed for both STI measurement systems, the following detailed description of the LVET and PEP timing and display mechanisms will apply equally, with the LVET reference numerals preceding the PEP reference numerals, respectively. One-microsecond monostables 30, 31, 32 and 33 shape the trigger pulses which activate the set and reset inputs to the RS flip-flops 36 and 37. Whenever a logical one pulse is received at the set input of RS flip-flop 36 or 37, the Q output changes to a logical level one state, thereby enabling the NAND gate 39 or 40, which permits 10 kilohertz clock pulses $\phi 1$ from the 10 kilohertz clock 42 to be strobed into the 12-bit BCD ripple counters 44 or 45 which divides its final total by ten through omission of the last four least significant bits (LSB) at the outputs. Immediately prior to the enabling of NAND gate 38 or 40, a one-microsecond pulse from monostable 31 or 33 also resets the contents of the BCD ripple counter 44 or 45. A logical one pulse arriving at the reset inputs of the RS flip-flops 36 or 37 returns the Q output to logical zero, thereby disabling NAND gates 39 or 40, which stops the clocking process. In the case of the LVET measurement, the 12-bit value of the BCD ripple counter 44 represents the total period for the LVET interval in terms of milliseconds since the number of clock pulses counted in that interval were divided by ten. In addition to stopping the timing process, the one microsecond reset pulse from monostable 30 acts as a write-enable command by momentarily enabling the WE input of 12-bit latch 46. The latch 46 thereupon immediately stores the contents of the 12-bit BCD ripple counter 44 wherein the 12-bit latch 46 acts as the LVET buffer memory 14 and the 12-bit BCD/10 ripple counter 44 and its accompanying logic circuitry act as the LVET digital timer 12 shown in FIG. 1. Likewise, by comparing FIG. 1 and FIG. 3, the PEP measurement system functions in the same manner as described above, with the 12-bit latch 47 acting as the PEP buffer memory 15 which has its WE input momentarily enabled by the one-microsecond reset and write-enable command pulse from monostable 32, thereby transferring the contents from 12-bit BCD/10 ripple counter 45. Along with its accompanying logical circuitry, the 12-bit BCD/10 ripple counter 45 acts as the PEP digital timer 13 which is also reset by the one-microsecond pulse from monostable 33. For display purposes, the outputs of both the LVET latch 46 and the PEP latch 47 are continually transmitted to the 12-bit BCD to 7-segment decoder/multiplexer circuits 48 and 49 wherein they provide three-decade 7-segment logical command levels A through G to the three digital numerals of the LVET multiplexed readout 20a and the PEP multiplexed readout 20b. The two outputs of the digit selector/multiplexer control logic 48a and 49a for selection of appropriate numerals in the multiplexed readouts 20a and 20b are energized by the DS inputs in coordination with the outputs from the 7-segment decoder/multiplexers 48 and 49, wherein the foregoing digital readout functions 20a and 20b are timed in synchrony with clock output $\phi 2$ from the 1 kilohertz clock 43.

The PEP/LVET ratio is computed by the 12-bit BCD counter/divider 50, which received gated clock pulses from NAND gates 39 and 40, stores them in its X and Y registers, performs a division operation with a programmed logic assembly while the DE input is enabled with a logical one divide-enable level command from RS flip-flop 36, and transfers its quotient to the 12-bit latch 51 during the one-microsecond write-enable command to the WE input from the monostable 30. Contents of the 12-bit counter/divider 50 are reset by the one-microsecond pulse from the monostable 33, which indicates commencement of the next PEP interval. As with the LVET and PEP multiplexed readouts 20a and 20b, the PEP/LVET multiplexed readout 20c displays the contents of the 12-bit latch 51 in conjunction with the 12-bit BCD to 7-segment decoder/multiplexer 52 and the digit selector/multiplexer 52a at a rate governed by clock output $\phi 2$ from the 1 kilohertz clock 43. Reference to both FIG. 1 and FIG. 3 again will illustrate that the 12-bit BCD counter/divider 50 acts as the ratio divider 18, and 12-bit latch 51 acts as the PEP/LVET buffer memory 19.

Whereas the 12-bit heart rate converter 53 has only a single input from the Schmitt trigger 21, a one-microsecond monostable 35 provides a pulse that is delayed one-microsecond after the one-microsecond monostable 34, thereby momentarily enabling the WE input of the 12-bit H.R. latch 54, allowing it to store the revised heart rate value. Input to the 12-bit heart rate converter 53 is supplied through NAND gate 41, which permits 10 kilohertz clock pulses $\phi 1$ to pass when a logical one level appears at the Q output of the RS flip-flop 38, thereby providing the input stage for heart rate converter 16 shown in FIG. 1. Since the pulses from Schmitt trigger 21 occur at the end of every cardiac systole, the multiplicative inverse of the interval between these pulses is directly proportional to the heart rate. The remaining circuitry for the heart rate converter 16 indicated in FIG. 1 is therefore a counter/shift register with its contents inverted and multiplied by 60,000 to convert beats/millisecond into beats/minute. Alternatively, a microprocessor with programmed logic assemblies (PLA) could be utilized to accomplish the same algebraic manipulations. As with LVET, PEP and PEP/LVET multiplexed readouts 20a, 20b and 20c, the heart rate multiplexed readout 20d displays the contents of the 12-bit latch 54 with the 12-bit BCD to 7-segment decoder/multiplexer 55 and digit selector/multiplexer 55a at a rate synchronized by the 1 kilohertz clock output $\phi 2$.

FIGS. 4a and 4b demonostrate the underlying mechanism of the deconvolver 5 depicted in FIGS. 1 and 3. Graphical portrayal of the magnitude spectrum for the transformed transient response wavelet |TRW(f)| 56a (FIG. 4a) associated with the fundamental mechanical-acoustical properties of heart action illustrates the bimodal form of its frequency distribution indicated by the solid curve. Magnitude spectrum |H(f)| 56b represented by the dashed curve, superposed with the graph 56a of |TRW(f)| in FIG. 4a, demonstrates the frequency distribution for the primary harmonic component. It is the unique purpose of the PCG deconvolver 5 comprising the method and system of the present invention to synthesize the system function DCV(f) with a corresponding magnitude spectrum |DCV(f)| 57 (see FIG. 4b) which is the multiplicative inverse or reciprocal of |TRW(f)| 56a for all values of frequency. Practical considerations of course limit values of frequency to those between 5 and 500 hertz. Otherwise, vibrational artifacts at frequencies lower than 5 hertz and electrical transients combined with Gaussian noise at frequencies higher than 500 hertz would cause interference with the deconvolution process. |DCV(f)| 57 (FIG. 4b) optimizes both theoretical and practical considerations for |TRW(f)| 56a and ultimately for the PCG output 4a. Even a casual visual inspection will reveal that the product of |TRW(f)| 56a with |DCV(f)| 57 remains at a constant value to within a high degree of accuracy.

Referring now to FIGS. 4a, 4b and 5a, the general form for an analog PCG deconvolver 5 system illustrated in block form in FIG. 1, and its mode of operation are clearly indicated. Fabrication of the PCG deconvolver 5, along with synthesis of its associated system function, DCV(f), of which its magnitude spectrum, |DCV(f)| 57 is shown in FIG. 4b, begins by applying the PCG output 4a to the filter network 58, said network having a transient response H(t) and a magnitude spectrum |H(f)| (dashed curve) 56a. The output of the filter network 58 is fed to the inverting input of high-performance operational amplifier A4a, which generates both the multiplicative and additive inverses of H(t) at its output through the closed loop negative feedback system provided by noise filter 59. The noise filter 59 also attenuates high-frequency Gaussian noise at a slew rate of 6db/octave. Concurrently, the positive feedback from the biasing and signal enhancement network 60 supplies the resonant peak necessary for final inversion of the "notch" 56c appearing in magnitude spectrum |TRW(f)| 56a (see FIG. 4a). Thereupon, the system depicted in FIG. 5a has a frequency response spectrum 57 duplicating |DCV(f)| (see FIG. 4b), while attenuating frequencies above 500 hertz at a slew rate of 6db/octave after passing through low-level noise rejection network 61 to supply the final PCG deconvolver output 5a. FIG. 5b schematically diagrams typical circuitry for achieving the deconvolved output 5a shown by the generalized system in FIG. 5a. Low-frequency inversion is accomplished with the bridged-T combination of 10K resistors R21 and R22 together with 1.06 microfarad capacitor C13.

High-frequency inversion is achieved with 0.013 microfarad input capacitor C14 while primary resonant Q-factor inversion of |H(f)| 56b is optimized with 68 K input damping resistor R20. The complex impedance supplied by the parallel R-C feedback network consisting of 6.8 K resistor R23 and 0.047 microfarad capacitor C15, forms the circuitry for noise filter 59 which halts high-frequency elevation beyond 500 hertz and also controls the overall gain of operational amplifier A4b. Circuitry for biasing and signal enhancement system 60 is supplied by the dual R-C networks composed of the 1 K resistor R25 with 1.04 microfarad capacitor C17, and 10 K resistor R24 with 0.316 microfarad capacitor C16. Together the dual R-C networks R25-C17 and R24-C16 provide phase-shifting and Q-factor enhancement at the non-inverting input of operational amplifier A4b as manifested by the resonant peak in magnitude spectrum |DCV(f)| 57. A low-level noise rejection system 61 is constructed with silicon switch diodes D5 and D6 which work together with the 560 ohm resistor R26 and the 0.58 microfarad capacitor C18 to form a parallel R-C network to attenuate frequencies beyond 500 hertz at the deconvolver output 5a. Notwithstanding the multitude of conceivable variations in circuitry that would be obvious to those skilled in the art, the schematic diagram of FIG. 5b represents an elaboration of the principal features for the system in FIG. 5a and demonstrates a preferred circuit configuration for the analog version of the PCG deconvolver 5 herein incorporated as an essential element of the embodiment of the method and system of the present invention.

Reference to FIG. 5c demonstrates the logic circuitry for the digital version of the PCG deconvolver 5 depicted in the analog circuit configuration by FIGS. 5a and 5b. Transformation of the analog PCG signal 4a into a 12-bit digital format is accomplished with the CMOS (complimentary MOS) large-scale integrated (LSI) circuitry of the 12-bit analog to digital converter 62 no less than 1000 times/second, in accordance with the Nyquist sampling theorem for the 500 hertz bandwidth of deconvolver 5. Only the ten most significant bits contained in the output register of the 12-bit A/D converter 62 are presented for transmission upon reception of a logical one read-enable command at its RE input, thereby dividing the PCG signal 4a by a factor of four to prevent over-ranging and simultaneously truncating low-level digital noise. The 10 kilohertz clock output $\phi 1$ of clock 42 provides a synchronization signal for the internal dual-slope integration and voltage controlled oscillator systems of the A/D converter 62. A 512-bit read-only memory (ROM) 64 consisting of NMOS (n-channel MOS) LSI circuitry contains fifty normalized 10-bit values for TRW(t), where it is sequenced in one millisecond increments from 0 to 49 milliseconds, and an address counter activated by read-enable commands to its RE input, the 512-bit ROM 64 sometimes being termed a programmed-ROM or PROM by those skilled in the art. The NMOS LSI circuitry of the 2048-bit PLA (programmed logic array) control inverse filter microprocessor 63 accesses to the 10-bit outputs of both the A/D converter 62 and the ROM 64 at a rate established by division of one megahertz clock signal $\phi 3$ to deconvolve the PCG signal 4a by repetitively employing the following microprogram algorithm written in the FORTRAN language for ease of interpretation:

0000 PCG DECONVOLUTION PROGRAM
0100 DIMENSION PCG(50), TRW(50)
0110 READ (64,600) (TRW(I),I=1,50)
0111 READ (62,600) (PCG(I),I=1,50)
0600 FORMAT (F3.0)
0120 DECONVOLVE PCG WITH REVERSED TRW USING SIMPSON'S RULE
0130 CONTINUE
0140 AMPE=0.0

```
0150 AMPO=0.0
0160 SUM ODD TERMS
0170 DO 190 I=1,49,2
0180 AMPO=TRW(50−I)*PCG(I)+AMPO
0190 CONTINUE
0200 AMPO=AMPO*4.0
0210 SUM EVEN TERMS
0220 DO 240 I=2,50,2
0230 AMPE=TRW(52-I)*PCG(I)+AMPE
0240 CONTINUE
0250 AMPE=AMPE*2.0
0260 AMP=(AMPE+AMPO)/3.0
0270 SHIFT PCG ADDRESS LOCATIONS
0280 DO 300 I=1,49
0290 PCG(I)=PCG(I+1)
0300 CONTINUE
0310 TRANSFER UPDATED PCG VALUE FROM A/D CONVERTER 62
0320 READ(62,600)PCG(50)
0330 TRANSMIT DECONVOLVED OUTPUT
0340 WRITE(A4,600)AMP
0350 GO TO 130
0360 END
```

Before commencement of the PCG deconvolution algorithm, the DIMENSION statement 0100 in the above microprogram allocates 50 words, each totalling 500 bits, for initialization of the digitized PCG and TRW values. I/O READ statements 0110 and 0111 cause a transfer to the memory of the PLA control inverse filter microprocessor 63. READ statements 0110 enables and sequences the 512-bit ROM 64 for an initialized first-in first-out (FIFO) transfer of its contents followed immediately by statement 0111 which enables the output of the A/D converter 62 for initialized storage of the first 50 digitized values of the PCG. Both READ statements transfer a 10-bit word in accordance with FORMAT statement 0600. CONTINUE statement 0130 simply provides a return point to bracket the PCG deconvolution microprogram loop. Two variables, AMPE and AMPO, are defined and initially set to zero by statements 0140 and 0150. The DO loop comprised of statements 0170, 0180, and 0190 performs the first step in the deconvolution process by employing a Wiener type inverse digital filter operation through an initialization reversal of TRW(I) in the product with the odd terms of PCG(I) and summed with variable AMPO. AMPO is then multiplied by a factor of four in statement 0200 to complete the partial integral sum for the odd terms defined by Simpson's rule. Statements 0220, 0230, and 0240 form a DO loop that performs exactly the same operations as the DO loop initiated by statement 0170 except that even initialized terms summated by variable AMPE are involved. AMPE is multiplied by a factor of two in statement 0250 and the final value for the Simpson integral is completed in statement 0260 which defines the mnemonic output variable AMP. Statements 0270 through 0300 shift the initialized values for the PCG(I) by one word and enable the A/D converter 62. The most current value of the PCG is then transferred and initialized to the memory of the PLA control inverse filter microprocessor by READ statement 0320 under control of FORMAT statement 0600. Final 10-bit output AMP of the PCG deconvolution microprogram appears as a result of the WRITE I/O transfer statement 0340. Return to CONTINUE statement 0130 is accomplished with the GO TO statement 0350, thereby repeating the deconvolution microprogram loop until clock $\phi 3$ stops, whereupon control of the microprogram is transferred to statement 0000 for restart procedures.

A revised digital value (AMP) for the deconvolved PCG signal 4a appears at the 10-bit output of the PLA control inverse filter microprocessor 63 every millisecond and interfaces with the 10-bit digital to analog conversion ladder $R_o$ through $R_o \times 2^9$, which converges upon the inverting input of the summating operational amplifier A4c while 1.2 K resistor R28 stabilizes D.C. offset bias. Conversion ladder resistor $R_o$ has a value of 1 K and therefore $R_o \times 2^9$ equals 512 K. The complex impedance provided by the parallel R-C feedback network consisting of 1 K resistor R27 and 0.33 microfarad capacitor C19, controls the overall gain of the summating resistor input ladder $R_o$ through $R_o \times 2^9$ and attenuates both high-frequency analog and digital switching noise above 500 hertz at a slew rate of 6db/octave. Silicon switch diode D7 rejects low-level noise at all frequencies while the 560 ohm resistor R29 and the 0.58 microfarad capacitor C20 form a parallel R-C network to further attenuate high-frequencies beyond 500 hertz at the PCG deconvolver output 5a.

It is to be noted in connection with the foregoing that the amplifiers A4a, A4b, and A4c are identical high performance operational amplifiers with internal frequency compensation.

With particular reference to the method and system depicted in FIG. 1, it should be noted that the ratio divider 18 can be programmed to compute an averaged value for the PEP/LVET ratio over two or more systolic cycles. Such an average could be useful in conjunction with associated regression formulae for calculation of stroke index, cardiac index, ejection fraction, and cardiac output. In a similar fashion, output from the LVET timer 12 and the PEP timer 13 could also be averaged over two or more systolic cycles as a means of stabilizing anomalous variations.

This application is related to Disclosure Document No. 048742 titled Phonocardiogram Deconvolver Device for Rapid Non-invasive Determination of the Systolic Time Intervals.

While I have illustrated and described herein only two forms in which my invention can conveniently be embodied in practice, it is to be understood that these embodiments are given by way of example only, and not in a limiting sense. The invention, in brief, comprises all the embodiments and modifications coming with the scope and spirits of the following claims.

I claim:

1. A system for deconvolving the phonocardiogram (PCG) to extract the systolic valvular events, SVE(t), from said PCG for determination of the systolic time intervals (STI), comprising:
   transducer means for converting heart sounds into an electrical phonocardiogram (PCG), electrical means having a transfer function matching the inverse of the Fourier transformation for the transient response wavelet, TRW(f), associated with the fundamental mechanical-acoustical properties of the heart as transduced by said transducer means
   means applying said PCG to said electrical means
   further means responsive to signals produced by said electrical means for generating signals corresponding to said SVE(t) to define the temporal boundaries of the STI.

2. The system as defined in claim 1 wherein said further means comprises analog circuitry.

3. The system as defined in claim 1 wherein said further means comprises digital circuitry.

4. The system as defined in claim 1 wherein said further means comprises
 (a) means for converting said deconvolved PCG signal to a signal of uniform polarity;
 (b) means for separating and identifying from said converted signal temporal boundaries defining the PEP and LVET;
 (c) means for computing values of the PEP and LVET.

5. A system for the non-invasive determination of systolic time intervals as defined in claim 9 including equalization circuit means for correcting any phase or frequency distortion introduced into said PCG signal by said transducer means.

6. A system for the non-invasive determination of systolic time intervals as defined in claim 9 wherein said means for separating and identifying further defines the heart pulse interval for measurement of the heart rate.

7. A system for the non-invasive determination of systolic time intervals as defined in claim 9 wherein said means for computing the values of the PEP and LVET comprises a combination of microprocessor and programmed logic assembly integrated circuitry for providing real time computation of the values for PEP and LVET.

8. A method for extracting systolic valvular events, SVE(t), from heart sounds for determination of the systolic time intervals (STI), which comprises:
 (a) transducing the heart sounds into an electrical phonocardiogram signal;
 (b) deriving from the aforesaid signal the transient response wavelet, TRW(t) and its Fourier transformation, TRW(f), for the heart from the fundamental mechanical-acoustical properties of the biophysical cardiac system;
 (c) matching said phonocardiogram signal with a system function which is the inverse of said Fourier transformation, TRW(f), over a predetermined range of frequencies, and finally;
 (d) generating an electrical output from said matched inverse system function which corresponds to the onset of said transient response wavelet, TRW(t), resulting from initial cardial contraction and aortic valvular events that temporally define boundaries for said STI.

9. The method as set forth in claim 8 wherein the averaged analytical expression for said TRW(t) is as follows:

$$TRW(t) = 3Ae^{-t/0.012} \sin 2(65)t - Ae^{-t/0.015} \sin 2(100)t$$

(where A = SVE(0), and t is in seconds).

* * * * *